(12) United States Patent
Leduc et al.

(10) Patent No.: US 9,447,003 B2
(45) Date of Patent: Sep. 20, 2016

(54) METHOD FOR SYNTHESISING TRIFLUOROETHYLENE FROM CHLOROTRIFLUOROETHYLENE

(71) Applicant: ARKEMA FRANCE, Colombes (FR)

(72) Inventors: Philippe Leduc, Larajasse (FR); Thierry Lannuzel, Villeurbanne (FR); Dominique Garrait, Charly (FR); Serge Hub, Villeurbanne (FR); Emmanuel Guiraud, Saint-Genis Laval (FR); Fabrice Domingues Dos Santos, Lyons (FR)

(73) Assignee: ARKEMA FRANCE, Colombes (FR)

( * ) Notice: Subject to any disclaimer, the term of this patent is extended or adjusted under 35 U.S.C. 154(b) by 5 days.

(21) Appl. No.: 14/381,247

(22) PCT Filed: Feb. 22, 2013

(86) PCT No.: PCT/FR2013/050373
§ 371 (c)(1),
(2) Date: Aug. 27, 2014

(87) PCT Pub. No.: WO2013/128102
PCT Pub. Date: Sep. 6, 2013

(65) Prior Publication Data
US 2015/0094432 A1    Apr. 2, 2015

(30) Foreign Application Priority Data
Feb. 28, 2012 (FR) .................................... 1251784

(51) Int. Cl.
*C07C 17/23*     (2006.01)
*C08F 214/22*    (2006.01)
*B01J 35/10*     (2006.01)
*B01J 23/44*     (2006.01)
*C07C 17/383*    (2006.01)
*H01L 41/45*     (2013.01)
*H01L 41/193*    (2006.01)

(52) U.S. Cl.
CPC ............... *C07C 17/23* (2013.01); *B01J 23/44* (2013.01); *B01J 35/1009* (2013.01); *B01J 35/1042* (2013.01); *C07C 17/383* (2013.01); *C08F 214/22* (2013.01); *H01L 41/45* (2013.01); *H01L 41/193* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,802,887 A | * | 8/1957 | Smith | C07C 17/23 570/156 |
| 3,564,064 A | | 2/1971 | Nakagawa | |
| 3,581,466 A | * | 6/1971 | Rudolph | C07C 17/38 95/180 |
| 4,061,849 A | * | 12/1977 | Muenster | B01D 53/1487 203/42 |
| 4,736,006 A | * | 4/1988 | Reimschuessel | C08F 210/02 526/247 |
| 5,159,037 A | * | 10/1992 | Clement | C07C 43/17 526/242 |
| 2003/0157009 A1 | * | 8/2003 | Corr | C07C 17/389 423/240 S |
| 2008/0081195 A1 | | 4/2008 | Chung et al. | |

FOREIGN PATENT DOCUMENTS

| | | | | |
|---|---|---|---|---|
| GB | 990805 A | * | 5/1965 | ............... C07C 7/11 |
| WO | WO 2006033771 A2 | * | 3/2006 | ............. C07C 17/04 |
| WO | WO 2013113785 A1 | * | 8/2013 | ........... C07C 17/354 |

OTHER PUBLICATIONS

Feiring et al., "Trifluoroethylene deflagration", Chemical & Engineering News, 1997, vol. 75, No. 51, p. 6.*
International Search Report dated May 29, 2013 issued in corresponding PCT/FR2013/050373 application (pp. 1-2).

* cited by examiner

*Primary Examiner* — Nicole M Buie-Hatcher
(74) *Attorney, Agent, or Firm* — Millen, White, Zelano and Branigan, P.C.

(57) ABSTRACT

The present invention relates to the preparation of trifluoroethylene ($VF_3$ or TrFE) by hydrogenolyzis of chlorotrifluoroethylene (CTFE) in the gaseous phase over a group VIII metal catalyst deposited on a support. This method can be used to obtain $VF_3$ in an economical manner in conditions which minimize the risk of explosion of this molecule. Using a catalyst containing a group VIII metal and, more specifically, containing Pd deposited on a support and a specific series of steps of separation and purification makes it possible to obtain excellent CTFE conversion rates and high selectivity in $VF_3$ at atmospheric pressure and at low temperatures.

15 Claims, 2 Drawing Sheets

METHOD FOR SYNTHESISING TRIFLUOROETHYLENE FROM CHLOROTRIFLUOROETHYLENE

FIELD OF THE INVENTION

The present invention relates to the field of unsaturated fluorohydrocarbons and has more particularly a subject matter of the preparation of trifluoroethylene ($VF_3$ or TrFE) by hydrogenolysis of chlorotrifluoroethylene in the gas phase over a catalyst of a metal from Group VIII deposited on a support.

TECHNICAL BACKGROUND

Fluoro-olefins, such as $VF_3$, are known and are used as monomers or comonomers in the manufacture of fluorocarbon polymers exhibiting noteworthy characteristics, in particular an excellent chemical strength and a good thermal resistance.

Trifluoroethylene is a gas under standard pressure and temperature conditions. The main risks related to the use of this product relate to its flammability, its propensity to self-polymerization when it is not stabilized, its explosiveness due to its chemical instability and its supposed sensitivity to peroxidation, by analogy with other halogenated olefins. Trifluoroethylene exhibits the distinguishing feature of being extremely flammable, with a lower explosive limit (LEL) of approximately 10% and an upper explosive limit (UEL) of approximately 30%. However, the major danger is associated with the propensity of $VF_3$ to violently and explosively decompose under certain pressure conditions in the presence of an energy source, even in the absence of oxygen. Tests carried out by the applicant company in order to determine the limiting stability pressure (Pst) of $VF_3$ (maximum pressure for which there is no ignition) have made it possible to determine the Pst of $VF_3$ at 4 bar. In the event of explosion, under the conditions of the test, the Pex/Pi excess pressure ratio is approximately 10. For its part, the minimum ignition energy is unknown. This is why it is essential to avoid any point heat source, such as that resulting from the uncontrolled exothermic polymerization (self-polymerization). Finally, as $VF_3$ is a halogenated ethylenic compound, it is included among the peroxidizable compounds. The risk of peroxidation and also the risk of self-polymerization increase in the presence of a liquid phase. There is a risk of explosion as a result of a peroxidation or of an initiation of polymerization during the storage of this type of molecule.

In view of the main risks above, the synthesis and the storage of $VF_3$ present specific problems and impose strict safety rules throughout these processes.

Several routes for the synthesis of $VF_3$ are described in the literature.

A first route, for example described in the document EP 485 246, consists of the hydrogenolysis of 1,1,2-trichloro-1,2,2-trifluoroethane (CFC-113) carried out in the gas phase in the presence of a mixed catalyst based on copper or on silver and on at least one metal from the platinum group (ruthenium, rhodium, palladium, osmium, iridium or platinum). While the starting materials are readily available, the main product from this technique is CTFE, $VF_3$ being only a byproduct. The lifetime of these catalysts is relatively short and it is difficult to obtain good selectivity for $VF_3$ if the conversion of the CFC-113 is increased. The $VF_3$ yields are thus low.

A second route for the preparation of trifluoroethylene is based on the catalytic dehydrofluorination of tetrafluoroethane HFC-134a. The document FR 2 729 136 thus describes a process which employs aluminum fluoride as catalyst. The trifluoroethylene is obtained by catalytic dehydrofluorination in the presence of $BF_3$. The degree of conversion of the HFC-134a is 18.5%. The costs of the catalyst for this technique are low and there is no need to inject hydrogen, which simplifies the collection of products. However, the operating conditions are difficult and the degree of conversion of the HFC-134a is low, just like the trifluoroethylene yield.

A third route for the preparation of trifluoroethylene is represented by the debromination/dechlorination reaction of 1,1,2-trifluoro-2-chloro-1-bromoethane, described, for example, in document JP57026629. The reaction takes place in the presence of water and of a dehalogenating agent (for example Zn). The reaction conditions are mild, but the starting materials are difficult to find and the reaction produces a great deal of effluents.

A fourth route for the preparation of trifluoroethylene, for example described in the document U.S. Pat. No. 5,892,135, resorts to saturated halogenated hydrocarbons of $CF_3CClFX$ type (X being H, Cl or F), such as 124, 114a and 115, in the presence of a catalyst composed of one or more metal elements, such as Ru, Cu, Ni, Cr, or of their metal oxides or halides. The degree of conversion of the $CF_3CClFX$ can reach 91%, while the selectivity of trifluoroethylene can reach 83%, the remainder being 1132a, HFC-134a and 1122. This technique for the manufacture of trifluoroethylene exhibits a relatively high yield; however, the reaction temperature is high (between 325-425° C.) and the catalyst easily loses its activity. It also exhibits difficulties in collecting, separating and purifying the reaction products.

A fifth known route for the preparation of trifluoroethylene uses, as starting materials, chlorotrifluoroethylene (CTFE) and hydrogen in the presence of a catalyst having, as active components, metals from Group VIII and a support composed of porous materials, such as active charcoal, alumina, titanium oxide, magnesium oxide, magnesium fluoride and aluminum fluoride.

The catalytic hydrogenolysis of CTFE is generally carried out in the gas phase. For example, the document U.S. Pat. No. 3,564,064 describes a catalyst based on Pd or Pt on a support of active charcoal or alumina. The reaction temperature is between 200 and 320° C., with a contact time of 0.1 to 4 seconds. The gases resulting from the reaction are washed in water and a base and then dried with anhydrous calcium sulfate. The products are recovered by condensation in a trap cooled by a methanol/dry ice mixture and are then purified by fractional distillation of the mixture recovered in the trap cooled by acetone/dry ice. The degree of conversion of the CTFE is more than 60%, with a selectivity for $VF_3$ of more than 80%.

However, the catalytic hydrogenolysis of CTFE can be carried out in the liquid phase in the presence of a hydrochloric acid acceptor and of a metal from Group VIII, as described in the document CN 1 080 277. The acid receptor is an alcohol, an amine, an ester or an ether; the degree of conversion of the CTFE reaches 100%, with a selectivity for $VF_3$ of 80-90% and a yield of 60-90%. In addition to the trifluoroethylene, difluoroethylene, 1,1,2-trifluoroethane and 1,1-difluoroethane are obtained as byproducts.

On comparing the technique for the production of trifluoroethylene from CTFE with that which starts from CFC-113, there is a decrease in the reaction products, with a relatively large increase in the trifluoroethylene yield; however, problems of lifetime of the catalyst and the difficulties in collecting, separating and purifying mentioned for the other routes also exist with this technique. In point of fact, these stages have to be compatible with the reaction being carried out on an industrial scale.

There thus exists a real need to develop an alternative process for the preparation of trifluoroethylene from CTFE which makes it possible to overcome the above-mentioned disadvantages so as to obtain $VF_3$ in an economical manner under conditions which limit as far as possible the risks of explosiveness of this molecule.

It has now been found that, for the hydrogenolysis of CTFE, the use of a catalyst based on a metal from Group VIII and more particularly based on Pd deposited on a support and also a particular sequence of separation and purification stages makes it possible, at atmospheric pressure and at relatively low temperatures, to obtain excellent degrees of conversion of the CTFE and of selectivity for $VF_3$.

SUMMARY OF THE INVENTION

A subject matter of the present invention is thus a process for the manufacture of trifluoroethylene ($VF_3$) from chlorotrifluoroethylene (CTFE), said process comprising the following stages, carried out at atmospheric pressure:
i) introducing, into a reaction space, a mixture A consisting of hydrogen, CTFE and optionally an inert gas, such as, for example, nitrogen, in the gas phase over a bed of catalyst based on a metal from Group VIII deposited on a support, the $H_2$/CTFE molar ratio ranging from 0.5/1 to 2/1. The temperature of the reactor is controlled by the circulation in a jacket of a heat-exchange fluid maintained at a temperature of between 25 and 50° C., resulting, after a sufficient contact time, in the achievement of a gas mixture B composed of the reaction products comprising $VF_3$ and organic byproducts, and also unconsumed $H_2$, optional inert gas and unconsumed CTFE and hydracids;
ii) removing the hydracids present in the mixture B by washing with water, followed by washing with a dilute base and then drying, resulting in the recovery of a gas mixture C composed of reaction products comprising $VF_3$ and organic byproducts, and also unconsumed $H_2$, inert gas (if present) and unconsumed CTFE;
iii) passing the gas mixture C through a countercurrentwise column of a solvent, at a temperature lower than ambient temperature, resulting in the achievement, on the one hand, of the hydrogen and the inert gas (if present) and, on the other hand, of a mixture composed of organic products dissolved in said solvent;
iv) desorbing, by heating to boiling point, the organic products dissolved in the solvent in order to obtain, on the one hand, the solvent, which will be recycled to the absorption, and, on the other hand, a mixture D composed of the reaction products devoid of hydrogen and of other inert gases (if present);
v) distilling said mixture D of organic products on a first column, resulting in the recovery of the $VF_3$ at the column top and of a mixture E at the column bottom composed of unconverted CTFE and also reaction byproducts;
vi) distilling said mixture E in order to recover and recycle the unconverted CTFE at the column top and to remove the reaction byproducts at the bottom of this second column.

The process forming the subject matter of the present invention exhibits the advantage of achieving a very high conversion to give $VF_3$ (up to 80%), with a selectivity for $VF_3$ ranging up to 80%, while limiting as far as possible the risks of explosiveness of this molecule and considerably reducing the reaction temperature, so as to be able to effectively apply it on an industrial scale.

BRIEF DESCRIPTION OF THE DRAWINGS

Other characteristics and advantages will emerge from the detailed description of the process for the manufacture of $VF_3$ from CTFE according to the invention which will follow and from the appended figures, in which.

DETAILED DESCRIPTION OF THE INVENTION

Figure 1:
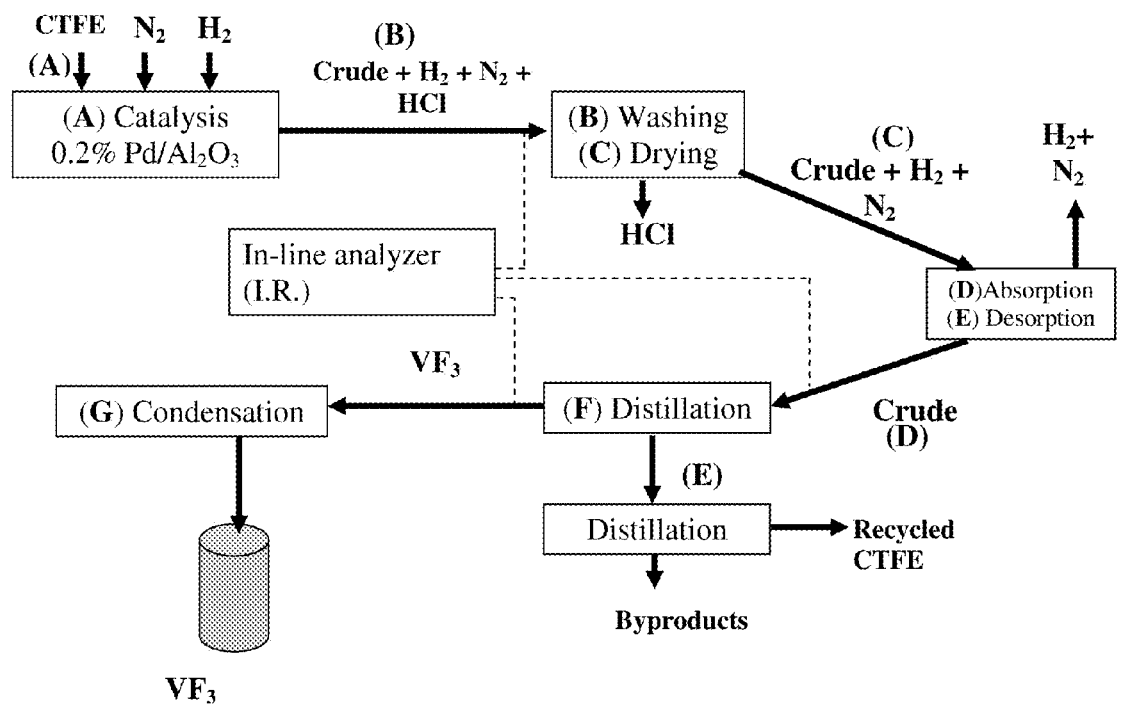
FIG. 1 diagrammatically illustrates all the stages of manufacture of $VF_3$ from CTFE.

The process according to the invention, represented diagrammatically in the appended FIG. 1, is based on the reaction for the synthesis of $VF_3$ by hydrogenolysis of CTFE. The reaction is carried out over a catalyst based on a metal from Group VIII deposited on a support. The metals from Group VIII which are suitable for this reaction are chosen from Pd, Pt, Rh and Ru. The support of the catalyst is chosen from active charcoal, alumina and calcium carbonate.

According to one embodiment, the reaction is carried out over a catalyst based on palladium deposited on $Al_2O_3$, such as that sold by Johnson Matthey under the reference: 0.2R463 Palladium on Alumina pellets Type 463.

The process consists in simultaneously introducing hydrogen, the CTFE and optionally an inert gas, such as nitrogen, (forming the mixture A) in the gas phase over a bed of catalyst, the temperature of which is controlled by circulation, in the jacket of the reactor, of a heat-exchange fluid maintained between 25 and 50° C. The $H_2$/CTFE molar ratio is between 0.5/1 and 2/1 and preferably between 1/1 and 1.2/1. The nitrogen/$H_2$ molar ratio is between 0/1 and 2/1 and preferably between 0/1 and 1/1.

The contact time, calculated as being the ratio of the volume, in liters, of catalyst to the total flow rate of the gas mixture, in standard liters per second, at the inlet of the reactor, is between 10 and 30 seconds and preferably between 15 and 25 seconds.

Figure 2:
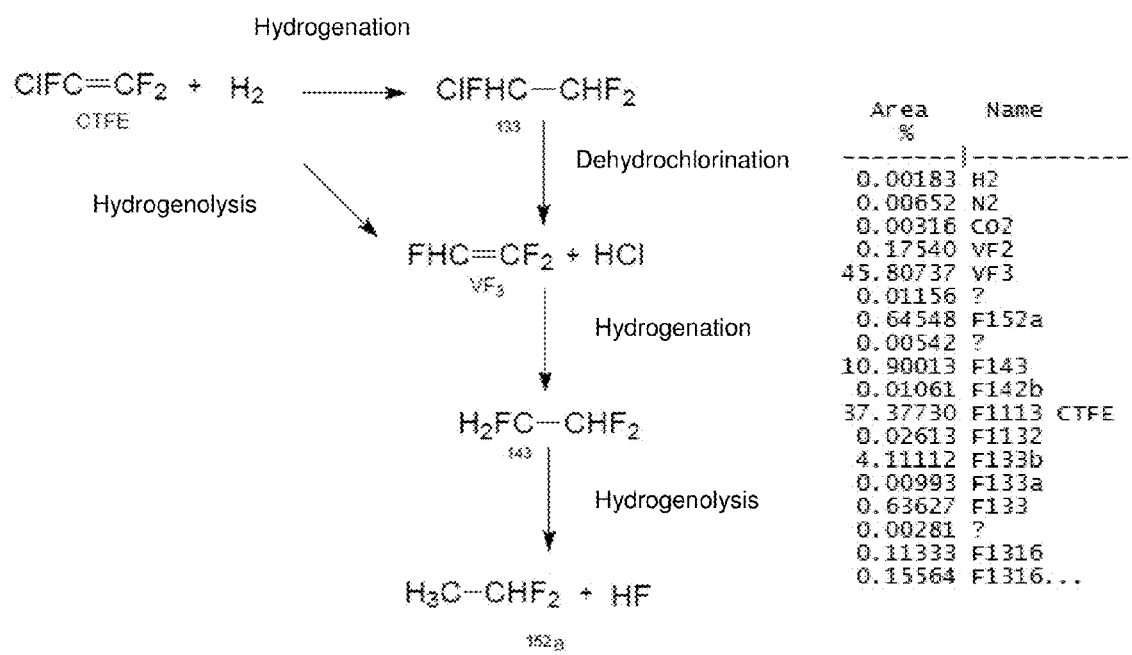
FIG. 2 illustrates the reaction scheme proposed in order to explain the presence of byproducts identified by chromatographic analysis.

The reaction is not complete; there thus remains hydrogen and CTFE mixed with the reaction products and the diluting nitrogen (if present) at the outlet of the hydrogenolysis reactor. The combination of these products forms the mixture B. The $VF_3$ is the main reaction product but byproducts are formed by secondary and/or successive reactions, as are shown by the chromatographic analysis of a test and the reaction scheme proposed for explaining the formation of these byproducts (appended FIG. 2).

At the outlet of the hydrogenolysis reactor, first the hydracids formed are removed. HCl and HF are absorbed in water in a washing column and the final traces of acid are removed by washing with a dilute base (NaOH or KOH). The remainder of the gas mixture, composed of the unconverted reactants ($H_2$ and CTFE), the diluting nitrogen (if present) and the reaction products ($VF_3$, 143, 133 and other organic products), which form the gas mixture C, is sent to a dryer in order to remove the traces of washing water. The drying is carried out using products such as calcium sulfate, sodium sulfate, magnesium sulfate, calcium chloride, potassium carbonate, silica gel or zeolites. In one embodiment, a molecular sieve (zeolite), such as siliporite, is used for the drying.

A stage of separating the hydrogen and the inert substances from the remainder of the other products present in the mixture C is subsequently carried out by absorption/desorption in the presence of an alcohol comprising from 1 to 4 carbon atoms and preferably ethanol, at atmospheric pressure and at a temperature below ambient temperature, preferably below 10° C. and more preferably still at a temperature of −25° C., for the absorption. In one embodiment, the absorption of the organic products is carried out in a countercurrentwise column with ethanol cooled to −25° C. The ethanol flow rate is adjusted as a function of the flow rate of organic products to be absorbed. The hydrogen and the inert gases, which are insoluble in ethanol at this temperature, are removed at the absorption column top. The organic products are subsequently recovered in the form of a gas mixture D by heating the ethanol to its boiling point (desorption), in order to be subsequently distilled.

This stage of hydrogen+inert substances/organic compounds present in the mixture C separation is thus carried out by bringing into direct contact with the solvent, unlike the separation methods known for mixtures of this type based on the condensation of the organic products in a trap cooled by a dry ice/solvent (acetone or methanol) mixture.

The pure $VF_3$ is subsequently distilled from the mixture D in order to be separated from the other organic products (CTFE, F143, F133 and other organic products, forming a mixture E). The distillation of the mixture D is carried out at atmospheric pressure and at a temperature of between −70° C. in the condensation and −30° C. in the boiler. In one embodiment, the distillation is of the cryogenic type carried out with equipment made of glass; the column used is, for example, a column of the Oldershaw type.

The pure $VF_3$ exiting at the column top is recovered by condensation in exchangers and intermediate storage tanks maintained at −80° C. at atmospheric pressure.

The mixture E comprising the other organic compounds is recovered at the column bottom. The distillation of said mixture E on a second column makes it possible to recover and recycle the unconverted CTFE at the column top and to remove the reaction byproducts at the bottom of this second column.

The process of the preparation of $VF_3$ according to the invention makes it possible to obtain a degree of conversion of the CTFE of between 60 and 80%, with a selectivity for $VF_3$ of between 50 and 80%.

The pure $VF_3$ which is recovered in the intermediate storage tank which acts as distillation receiver is subsequently transferred into a conditioning drum. According to one embodiment, the process of the invention comprises an additional stage of storage of the $VF_3$ obtained in stage v) in the presence of an amount of limonene sufficient to stabilize it at a maximum temperature of 50° C. The process for the preparation of $VF_3$ by hydrogenolysis of chlorotrifluoroethylene according to the invention, carried out with the continuous sequence of the different stages under chosen operating conditions (atmospheric pressure, low temperature), makes it possible to produce $VF_3$ while preventing the problems posed by its physicochemical (inflammability, reactivity and explosiveness) properties. This objective is achieved in particular by virtue of the stage of separation of hydrogen and inert gases (if present) from the organic compounds by absorption/desorption with a solvent, such as ethanol. The reaction products, thus freed from the noncondensible materials (unconverted hydrogen, inert substances, and the like), can subsequently be easily distilled at atmospheric pressure and at low temperature.

Other advantages of the process according to the invention are listed below:
  it makes it possible to recover pure $VF_3$ under conditions which make it possible to limit as far as possible the risks of explosiveness of this molecule;
  it makes it possible to manufacture $VF_3$ economically, under conditions such that the risks of explosiveness of this molecule are avoided;
  it makes it possible, by adjusting the distillation conditions, to obtain, at the column top, a mixture of $VF_3$ and CTFE comprising a predetermined proportion of CTFE which will be directly usable in polymerization. The optional concomitant presence of 143a, the reaction byproduct entrained at the column top with the CTFE, is not a disadvantage as this compound is inert with regard to the polymerization.

The $VF_3$ obtained following the process of the invention is used in particular as monomer or comonomer in the manufacture of fluorocarbon polymers. The comonomers capable of being copolymerized with $VF_3$ are in particular partially or completely fluorinated olefins. Mention may be made, as nonlimiting examples, of tetrafluoroethylene, chlorotrifluoroethylene (CTFE), hexafluoropropylene (HFP), 1,1,3,3,3-pentafluoropropene, vinyl fluoride, vinylidene fluoride ($VF_2$) and 2,3,3,3-tetrafluoropropene. Mention may in particular be made, among the other halogenated olefins capable of being copolymerized with $VF_2$ and $VF_3$, of CTFE, HFP and 1,1-chlorofluoroethylene (CFE).

The invention also relates to the process for the preparation of a fluorinated copolymer or terpolymer comprising, as monomer, $VF_3$ and, as comonomer, at least one partially or completely fluorinated olefin, said process comprising, beforehand, the synthesis of $VF_3$ according to the stages described above.

According to one embodiment, the invention relates to a process for the preparation of a fluorinated copolymer or terpolymer comprising, as monomers, $VF_3$, CTFE and optionally a partially or completely fluorinated olefin, in which the mixture of $VF_3$ and CTFE is obtained directly at the outlet of the distillation stage of the process for the synthesis of $VF_3$ described above. The advantage of such a process is that of avoiding the preparation and the homogenization of a mixture produced from the pure components, thus simplifying the operations prior to the polymerization.

In particular, the $VF_3$, where it is polymerized in the presence of vinylidene fluoride and optionally of at least one other halogenated olefin, makes it possible to obtain electroactive partially fluorinated copolymers or terpolymers having particularly advantageous electrical properties, such as the poly($VF_3$/$VF_2$/CFE) terpolymer. The materials obtained from these copolymers and terpolymers are then piezoelectric, pyroelectric and/or electrostrictive. The films produced from these copolymers or terpolymers have the characteristics typical of a relaxor ferroelectric: low hysteresis, high dielectric permittivity, strong deformation.

$VF_3$/$VF_2$/CFE terpolymers, their process of preparation and their use in the preparation of piezoelectric composite materials are described in the document US 2008/0081195.

The following examples illustrate the invention without limiting it.

Example 1

Test of the Performances of the Catalysts

Preparation of the Catalytic Charge

The bed of catalyst to be tested is inserted between two layers of inert substances, such as corindon or silica. In order, a first layer of corindon is introduced, over a height of 50 cm, into a tubular reactor consisting of a stainless steel tube with a length of 1200 mm over a diameter of 25 mm equipped with a jacket. A layer representing 100 cm³ of test catalyst is subsequently introduced onto this layer and then corindon is again introduced above the layer of catalyst until the reaction tube is completely filled.

The catalyst thus charged is subsequently activated under a stream of hydrogen in the following way: the reaction tube is placed in a tubular furnace and is fed via the top with a stream of hydrogen of 2 mol/h. The furnace is then heated up to 400° C. and the system is left under the same stream of hydrogen for 12 h. After this period of activation at 400° C. (chemical reduction of the catalyst), the tube is cooled to ambient temperature under a stream of hydrogen and is then isolated in order to be subsequently installed on a hydrogenolysis test bed.

Reaction for the Hydrogenolysis of CTFE:

The reaction tube charged with the activated catalyst is installed on a hydrogenolysis bed comprising:
  a CTFE feed controlled by a mass flow meter;
  a hydrogen feed controlled by a mass flow meter;
  an inert substance (in the case in point nitrogen) feed controlled by a mass flow meter;
  a feed for the jacket of a heat-exchange fluid, the temperature of which is regulated by a thermostatically controlled bath;
  a system for withdrawing the reaction products which makes it possible to carry out the analyses necessary for the calculation of the degrees of conversion of the CTFE and of the $H_2$, on the one hand, and of the selectivity for $VF_3$, on the other hand.

The operating conditions and results obtained with various types of catalytic charges are collated in table 1.

The physicochemical characteristics of the catalysts tested are as follows:
Catalysts on $Al_2O_3$: BET specific surface of approximately 5 m²/g and pore volume <0.1 cm³/g
Catalyst on C: BET specific surface of approximately 1600 m²/g and pore volume of approximately 1 cm³/g.

Example 2

Implementation of the Process According to the Invention

The micropilot plant represented diagrammatically in FIG. 1 was operated in the following way:
  4 hydrogenolysis reactors (A), each composed of a metal tube made of stainless steel with a length of 1200 mm and with a diameter of 25 mm, equipped with a jacket over the entire length of the tube, are charged with the following mixture:
    66 ml (110 g) of corindon;
    275 ml (436 g) of 0.2% $Pd/Al_2O_3$ catalyst (BET specific surface=5.3 m²/g and a pore volume <1 cm³/g);
    45 ml (78 g) of corindon.
  the catalytic composition is reduced at 250° C. for 6 hours by a flow rate of 1 mol/h of hydrogen.
  the jacket of each reactor is subsequently fed with a heat-exchange fluid thermostatically controlled at 25° C.
  each reactor is fed with 1 mol/h of CTFE and 1 mol/h of hydrogen. It is also possible to feed the reactors with an inert gas (in this case nitrogen).

The contact time, calculated as being the ratio of the volume in liters of catalyst to the sum of the flow rates of the reactants in standard liters per second, is of the order of 22 seconds.

The gases exiting from the 4 reactors are gathered together and introduced at the bottom of a column for scrubbing out the hydracids (B) composed of a tube made of fluoropolymer with a length of 355 mm and with a diameter of 40 mm packed with rings made of fluoropolymer with a diameter of 4 mm and with a length of 5 mm.

The scrubbing column is fed continuously with water at a flow rate of 10 l/h.

The water laden with hydracid is continuously removed at the bottom of the scrubbing column. The reaction products, thus freed from the hydracids, are subsequently sent to a drying section (C) composed of two metal tubes made of stainless steel with a length of 800 mm and with a diameter of 50 mm, mounted in series, filled with molecular sieve of the silliporite 3A type.

The gases, thus dried, are subsequently sent to an absorption column (D) composed of a metal tube made of stainless steel with a length of 700 mm and with a diameter of 40 mm

TABLE 1

| Catalyst | Test No. | Catalytic bed volume (ml) | $H_2$ flow rate (Sl/h) | CTFE flow rate (Sl/h) | $N_2$ flow rate (Sl/h) | Contact time (s) | Jacket temperature (° C.) | CTFE conversion (%) | $VF_3$ selectivity (%) |
|---|---|---|---|---|---|---|---|---|---|
| 0.2% $Pd/Al_2O_3$ | 1 | 100 | 8.6 | 8.6 | 0 | 21 | 100 | 48 | 56.5 |
| | 2 | 100 | 8.6 | 8.6 | 0 | 21 | 20 | 22 | 74.5 |
| | 3 | 100 | 8.6 | 8.6 | 0 | 21 | 50 | 49.2 | 52.1 |
| | 4 | 100 | 25.7 | 26 | 0 | 7 | 25 | 43 | 60.4 |
| | 5 | 100 | 12.9 | 13 | 13 | 9 | 15 | 22.6 | 80.1 |
| | 6 | 100 | 25.7 | 26 | 0 | 7 | 15 | 17.6 | 85.2 |
| 2.2% $Pd/Al_2O_3$ | 7 | 100 | 4.3 | 8.6 | 0 | 28 | 80 | 94 | 34.8 |
| | 8 | 100 | 4.3 | 4.3 | 0 | 42 | 80 | 39 | 43.2 |
| | 9 | 100 | 4.3 | 8.6 | 0 | 28 | 50 | 94 | 32.6 |
| | 10 | 100 | 4.3 | 4.3 | 0 | 42 | 20 | 44 | 72.1 |
| | 11 | 100 | 6 | 6 | 6 | 20 | 6 | 34 | 76.2 |
| | 12 | 100 | 8.5 | 6.5 | 0 | 24 | 20 | 36 | 64.7 |
| 1% Ru/C | 13 | 100 | 8.6 | 8.6 | 0 | 21 | 50 | 0.7 | 0.9 |
| | 14 | 100 | 8.6 | 8.6 | 0 | 21 | 250 | 16.2 | 67.4 |
| 0.8% Pd + 10% $Cu/Al_2O_3$ | 15 | 100 | 8.6 | 8.6 | 0 | 21 | 25 | 0 | 0 |
| | 16 | 100 | 8.6 | 8.6 | 0 | 21 | 350 | 8 | 70 | equipped with a jacket and packed with glass rings with a diameter of 4.3 mm and with a length of 4.5 mm. The absorption column is fed at the top with ethanol via a pump, the flow rate of which is 8 liters/hour. The jacket of the absorption column is fed with a heat-exchange fluid at −25° C.

The hydrogen and the inert substances exit at the top of the absorption column, whereas the reaction products, dissolved in the ethanol, exit at the bottom of the column and are sent to a desorption section (E) composed of a glass column with a length of 250 mm and with a diameter of 18 mm, packed with glass rings with a diameter of 4.3 mm and with a length of 4.5 mm, and of a 1 liter round-bottomed glass flask where the ethanol is brought to boiling point using a heating mantle.

The organic products resulting from the reaction are evaporated and leave the desorption section via the column top, whereas the ethanol, freed from the organic products, is picked up by the pump in order to be fed at the top of the absorption column (D).

The mixture of organic products resulting from the desorption section is subsequently sent to the distillation section (F) composed of a concentrating section, with a column comprising 15 plates of Oldershaw type with a diameter of 28 mm, and of a stripping section, with a column comprising 5 plates of Oldershaw type with a diameter of 28 mm.

The boiler of this distillation consists of a glass tank equipped with a jacket fed with a heat-exchange fluid at −30° C. The undesirable heavy products and the unconverted CTFE are extracted continuously, so as to retain an unchanging level in the boiler.

The concentrating column is surmounted by a glass reflux condenser fed with a heat-exchange fluid at −75° C. The pure $VF_3$ is recovered at the top of the exchanger, which behaves like a dephlegmator, and is finally sent to the receiving section (G) composed of metal tanks made of stainless steel equipped with jackets fed with a heat-exchange fluid maintained at −80° C.

Results of $VF_3$ production campaigns on this micropilot in continuous operation are collated in table 2.

In test 1, only two hydrogenolysis tubes are fed with CTFE and hydrogen. An ethanol flow rate of the absorption section of 3 kg/h at −20° C. is sufficient to separate the organic products from the unconverted hydrogen. In the distillation section, an exchanger temperature of −72° C. makes it possible to achieve a $VF_3$ purity of 98.65%. The $VF_3$ productive output is 38.1 g/h, which represents a crude yield of 23.8%, with respect to the CTFE introduced.

In test 2, 4 hydrogenolysis tubes operate in parallel and feed the remainder of the plant. In view of the flow rate of organic products to be treated, the absorption section is fed with 4 kg/h of ethanol cooled to −25° C. In the distillation section, the top exchanger is fed with a heat-exchange fluid at −78° C., which makes it possible to achieve a purity of the $VF_3$ of 98.96%. The productive output of the plant, conducted under these conditions, is 67.5 g/h of $VF_3$, i.e. a crude yield of 21%, with respect to the CTFE fed in.

In test 3, the 4 hydrogenolysis tubes are fed with nitrogen in addition to the reactants (CTFE and $H_2$). The presence of nitrogen does not modify the effectiveness of the separation of the absorption section fed with 4 kg/h of ethanol at −25° C. The conditions of the distillation section are modified so as to increase the degree of recovery of the $VF_3$. Thus, with a temperature in the boiler of −23° C. and a top exchanger at −75° C., the productive output is 92.5 g/h of $VF_3$ with a purity of 98.7%. The recycling of the unconverted CTFE makes it possible, under these conditions, to achieve a crude yield of 57.8%, with respect to the CTFE employed.

Example 3

Preparation of a $VF_2/VF_3$ Copolymer 396 g of $VF_3$ and 750 g of $VF_2$ are charged to a reactor containing 1862 g of demineralized water, 0.34 g of methylhydroxypropylcellulose and 1.8 g of dipropyl peroxydicarbonate. The reactor is then brought to the temperature of 44° C. The reaction starts and is reflected by a fall in the pressure of the reactor which is compensated for by continuous injection of water. When 700 g of water have been introduced, the injection of water is halted and the pressure falls down to 65 bar. The reactor is then heated to 65° C. and the pressure continues to fall. When the pressure reaches 38 bar, the reactor is cooled down and is then emptied. The reaction mixture collected is filtered and the cake obtained is washed 5 times in 3 l of clean water before being dried in an oven at 70° C. to constant weight. The composition of the resin, analyzed by $^1H$ NMR, is found to be equal to 31.2 mol % of $VF_3$. The thermal characterization by DSC reveals a ferroelectric resin with a Curie transition of 99.8° C. and a melting point of 151.2° C.

TABLE 2

| | Feed flow rate per reactor | | | | | | ABSORPTION | DISTILLATION | | Results | | |
|---|---|---|---|---|---|---|---|---|---|---|---|---|
| | $H_2$ | CTFE | | Hydrogenolysis | | | Ethanol | Boiler | | | $VF_3$ | $VF_3$ |
| Tests | flow rate (Sl/h) | flow rate (Sl/h) | $N_2$ flow rate (Sl/h) | Reactor number | Jacket temperature (° C.) | Contact time (sec) | Jacket temperature (° C.) | flow rate (kg/h) | temperature (° C.) | Exchanger temperature (° C.) | Continuous production duration (h) | productive output (g/h) | purity (% by weight) |
| 1 | 22.4 | 22.4 | 0 | 2 | 25 | 22.1 | −20 | 3 | −26 | −72 | 39 | 38.1 | 98.65 |
| 2 | 22.4 | 22.4 | 0 | 4 | 25 | 22.1 | −25 | 4 | −26 | −78 | 40 | 67.5 | 98.96 |
| 3 | 22.4 | 22.4 | 2 | 4 | 25 | 21.2 | −25 | 4 | −23 | −75 | 70 | 92.5 | 98.7 |

Example 4

Preparation of a $VF_2/VF_3/CFE$ Terpolymer

An initial charge of 360 g of a mixture composed of 68 mol % of $VF_2$ and of 32 mol % of $VF_3$ is introduced into a 4l stirred reactor charged with 2.5 l of demineralized water. The reactor is brought to a temperature of 44° C. and then the polymerization initiator is injected via a high pressure pump in the form of a mixture with water. An additional amount of water is then injected in order to bring the reactor to a pressure of approximately 90 bar. The polymerization reaction starts and has a tendency to bring about a fall in the pressure. The latter is kept constant by injection under pressure of a secondary compressed mixture of monomers. This mixture has the following molar composition: 58.15% of $VF_2$, 27.31% of $VF_3$ and 14.54% of CFE. During the polymerization, the temperature inside the reactor is maintained at a value of between 44 and 51° C. The reaction is continued for approximately 7 h until the flow rate for injection of the secondary mixture falls below 20 g/h. The polymer, recovered in the form of a solid powder in suspension in the water, has the following molar composition, evaluated by combining the analysis by $^{19}F$ NMR and the elemental assay of the element chlorine:

$VF_2$: 61.9%
$VF_3$: 29.4%
CFE: 8.7%

Its number-average molar mass is 350 000 g/mol and its melting point is 122.1° C.

Example 5

Preparation of a $VF_2/VF_3/CTFE$ Terpolymer from $VF_3/CTFE$ Mixtures Originating Directly from the Distillation of the $VF_3$ 327 g of VDF, 163 g of TrFE and 10 g of CTFE are charged to a stirred 3.5 l reactor containing 2.7 l of deionized water and 0.4 g of cellulose ester as dispersing agent. The 10 g of CTFE originate from the TrFE prepared according to the invention with an adjustment of the distillation conditions resulting in a content of 4 mol % of CTFE in the TrFE, assayed by gas chromatography. The reactor is then brought to the temperature of 46° C. The peroxydicarbonate initiator is subsequently injected and the reaction starts. The consumption of the monomers brings about a decrease in the pressure, which is compensated for by the continuous injection of a VDF/TrFE/CTFE mixture at a pressure of between 80 and 110 bar. The mixture, the molar composition of which is respectively 67/26/1, was prepared from pure VDF and from TrFE comprising 21 mol % of CTFE, obtained by the process of the invention and with an iodine adjustment of the distillation conditions. When an amount of 500 g of mixture has been introduced into the reactor, the injection is halted and the pressure is allowed to fall for 40 minutes. The reactor is then cooled and degassed of the residual monomers and then the product, in the form of a suspension (slurry), is discharged from the reactor. The slurry is filtered, washed several times with pure deionized water and filtered a final time, and then the wet powder is dried in an oven at 70° C. 720 g of dry powder are recovered. The $^1H$ and $^{19}F$ NMR analysis produced reveals the following molar composition:

$VF_2$: 69.8%
TrFE: 26.5%
CTFE: 3.7%.

The invention claimed is:

1. A process for the manufacture of trifluoroethylene ($VF_3$) from chlorotrifluoroethylene (CTFE), said process comprising the following stages, carried out at atmospheric pressure:
   i) introducing, into a reactor having a jacket filled with a heat-exchange fluid, the temperature of which is maintained at between 25 and 50° C., a gas mixture A composed of hydrogen, CTFE and optionally an inert gas over a bed of catalyst based on a metal from Group VIII deposited on a support, the $H_2/CTFE$ molar ratio ranging from 0.5/1 to 2/1, resulting, after a sufficient contact time, in the achievement of a gas mixture B composed of reaction products comprising $VF_3$ and organic byproducts, and also unconsumed $H_2$, said inert gas and unconsumed CTFE and hydracids;
   ii) removing the hydracids present in the mixture B by washing with water, followed by washing with a dilute base and then drying, resulting in the recovery of a gas mixture C composed of reaction products comprising $VF_3$ and organic byproducts, and also unconsumed $H_2$, said inert gas and unconsumed CTFE;
   iii) passing the gas mixture C through a countercurrentwise column of a solvent, at a temperature lower than ambient temperature, resulting in obtaining, on the one hand, of the hydrogen and the inert gas and, on the other hand, of a mixture composed of organic products dissolved in said solvent;
   iv) desorbing, by heating to boiling point, the organic products dissolved in the solvent in order to obtain, on the one hand, the solvent, which will be recycled to the absorption, and, on the other hand, a mixture D composed of the reaction products devoid of hydrogen and of inert gas;
   v) distilling said mixture D of organic products, resulting in the recovery of the $VF_3$ at the column top and of a mixture E at the column bottom composed of unconverted CTFE and also reaction byproducts.

2. The process as claimed in claim 1, additionally comprising vi) of distillation of said mixture E on a second column in order to recover and recycle the unconverted CTFE at the column top and to remove the reaction byproducts at the bottom of this second column.

3. The process as claimed in claim 1, additionally comprising storage of the $VF_3$ obtained in v) in the presence of an amount of limonene sufficient to stabilize the $VF_3$ at a maximum temperature of 50° C.

4. The process as claimed in claim 1, in which said metal is deposited on an alumina or active charcoal support.

5. The process as claimed in claim 1, in which the catalyst is based on Pd deposited on an alumina support.

6. The process as claimed in claim 1, in which the solvent used in iii) is an alcohol comprising from 1 to 4 carbon atoms.

7. The process as claimed in claim 6, wherein the alcohol is ethanol.

8. The process as claimed in claim 1, in which the drying of the mixture B after removing the hydracids is carried out over a molecular sieve.

9. The process as claimed in claim 8, wherein the molecular sieve is siliporite.

10. The process as claimed in claim 1, in which said inert gas is nitrogen at a nitrogen/$H_2$ molar ratio ranging from 0/1 to 2/1.

11. The process as claimed in claim 10, wherein the nitrogen/$H_2$ molar ratio is 0/1 to 1/1.

12. The process as claimed in claim 1, further comprising producing a fluorinated copolymer or terpolymer from, as monomer, said $VF_3$ and, as comonomer, at least one partially or completely fluorinated olefin.

13. The process as claimed in claim 12, in which said olefin is tetrafluoroethylene, chlorotrifluoroethylene, hexafluoropropylene, 1,1,3,3,3-pentafluoropropene, vinyl fluoride, vinylidene fluoride, 2,3,3,3-tetrafluoropropene or 1,1-chlorofluoroethylene.

14. The process as claimed in claim 12, resulting in poly($VF_3$/$VF_2$/CFE) terpolymer being obtained.

15. The process as claimed in claim 12, in which, said olefin being CTFE, the process results, at the end of stage v), in a mixture of $VF_3$ and CTFE being obtained at the distillation column top.

\* \* \* \* \*